US012746536B2

(12) United States Patent
Hodoshima et al.

(10) Patent No.: US 12,746,536 B2
(45) Date of Patent: Sep. 29, 2026

(54) COMPOSITE CATALYST, METHOD FOR PRODUCING COMPOSITE CATALYST, AND METHOD FOR PRODUCING LOWER OLEFINS

(71) Applicant: CHIYODA CORPORATION, Yokohama (JP)

(72) Inventors: Shinya Hodoshima, Yokohama (JP); Azusa Motomiya, Yokohama (JP)

(73) Assignee: CHIYODA CORPORATION, Yokohama (JP)

( * ) Notice: Subject to any disclaimer, the term of this patent is extended or adjusted under 35 U.S.C. 154(b) by 28 days.

(21) Appl. No.: 18/460,027

(22) Filed: Sep. 1, 2023

(65) Prior Publication Data

US 2023/0405562 A1 Dec. 21, 2023

Related U.S. Application Data

(63) Continuation of application No. PCT/JP2022/007338, filed on Feb. 22, 2022.

(30) Foreign Application Priority Data

Mar. 4, 2021 (JP) ................................ 2021-034495

(51) Int. Cl.
*B01J 29/46* (2006.01)
*B01J 35/31* (2024.01)
(Continued)

(52) U.S. Cl.
CPC ............... *B01J 29/46* (2013.01); *B01J 35/31* (2024.01); *B01J 35/613* (2024.01); *B01J 35/615* (2024.01);
(Continued)

(58) Field of Classification Search
CPC ... B01J 29/46; B01J 29/87; B01J 29/88; B01J 35/31; B01J 35/613; B01J 35/615;
(Continued)

(56) References Cited

U.S. PATENT DOCUMENTS

| | | | |
|---|---|---|---|
| 6,080,698 | A | 6/2000 | Zhang et al. |
| 10,300,467 | B2 | 5/2019 | Nesterenko et al. |

(Continued)

FOREIGN PATENT DOCUMENTS

| | | | |
|---|---|---|---|
| CN | 1222898 | A | 7/1999 |
| CN | 1223602 | A | 7/1999 |

(Continued)

OTHER PUBLICATIONS

SAIP Substantive Examination Report for corresponding SA Application No. 523450507; Issued on May 7, 2024; 17 pages.
(Continued)

*Primary Examiner* — In Suk C Bullock
*Assistant Examiner* — Jason Y Chong
(74) *Attorney, Agent, or Firm* — CANTOR COLBURN LLP

(57) ABSTRACT

Provided is a composite catalyst that contains a zeolite which is a crystalline aluminosilicate that contains gallium and iron and has a skeletal structure of an 8- to 12-membered ring; or a zeolite which is a crystalline aluminosilicate that contains iron but no gallium and has a skeletal structure of an 8- to 12-membered ring; silicon dioxide as a binder; and diphosphorus pentoxide.

8 Claims, 8 Drawing Sheets

(51) Int. Cl.

| | |
|---|---|
| ***B01J 35/61*** | (2024.01) |
| ***B01J 35/70*** | (2024.01) |
| ***B01J 37/00*** | (2006.01) |
| ***B01J 37/04*** | (2006.01) |
| ***B01J 37/08*** | (2006.01) |
| ***B01J 37/10*** | (2006.01) |
| ***B01J 37/28*** | (2006.01) |
| ***B01J 37/30*** | (2006.01) |
| ***C07C 4/06*** | (2006.01) |

(52) U.S. Cl.
CPC ............. *B01J 35/617* (2024.01); *B01J 35/70* (2024.01); *B01J 37/0018* (2013.01); *B01J 37/04* (2013.01); *B01J 37/082* (2013.01); *B01J 37/10* (2013.01); *B01J 37/28* (2013.01); *B01J 37/30* (2013.01); *C07C 4/06* (2013.01); *B01J 2235/00* (2024.01); *C07C 2529/68* (2013.01)

(58) Field of Classification Search
CPC ...... B01J 35/617; B01J 35/70; B01J 37/0009; B01J 37/0018; B01J 37/04; B01J 37/082; B01J 37/10; B01J 37/28; B01J 37/30; B01J 2235/00; B01J 2229/42; C07C 4/06; C07C 2529/68; C07C 11/04; C07C 11/05; C07C 11/06; C07C 11/08; C01B 39/065; C01B 39/40; C10G 2400/20
See application file for complete search history.

(56) References Cited

U.S. PATENT DOCUMENTS

| | | | | |
|---|---|---|---|---|
| 10,549,267 | B2 | 2/2020 | Hodoshima et al. | |
| 2002/0056662 | A1 | 5/2002 | Quesada et al. | |
| 2003/0018231 | A1 | 1/2003 | Xu et al. | |
| 2007/0293714 | A1* | 12/2007 | Long | B01J 29/80 502/73 |
| 2008/0308455 | A1 | 12/2008 | Long et al. | |
| 2017/0252731 | A1 | 9/2017 | Hodoshima et al. | |
| 2020/0087228 | A1* | 3/2020 | Fletcher | C10G 69/04 |

FOREIGN PATENT DOCUMENTS

| | | | |
|---|---|---|---|
| CN | 1376764 | A | 10/2002 |
| CN | 1292052 | C | 12/2006 |
| CN | 107108397 | A | 8/2017 |
| JP | H11157831 | A | 6/1999 |
| JP | 2002294254 | A | 10/2002 |
| JP | 2014024005 | A | 2/2014 |
| JP | 2014024006 | A | 2/2014 |
| JP | 2014024007 | A | 2/2014 |
| WO | 2016017794 | A1 | 2/2016 |

OTHER PUBLICATIONS

International Search Report for International Application No. PCT/JP2022/007338; Mailing Date, Apr. 26, 2022.
Li et al., "Effect of iron and phosphorus on HZSM-5 in catalytic cracking of 1-butene", Fuel Processing Technology, 2015, vol. 134, pp. 32-38.
PCT International Preliminary Report on Patentability with Written Opinion of the International Searching Authority corresponding to International Application No. PCT/JP2022/007338; Mailing Date, Apr. 26, 2022.
EPO Extended European Search Report for corresponding EP Application No. 22763066.2; Issued Mar. 12, 2025.
IPIN Office Action for corresponding IN Application No. 202337061870; Mailing Date, Dec. 7, 2023.
JPO Notification of Reasons for Refusal for corresponding JP Application No. 2021-034495; Issued Apr. 8, 2025.
ID IPR Office Action for corresponding Indonesian Applicant No. P00202309386; Issued Mar. 26, 2025.
SIPO First Office Action for corresponding CN Application No. 202280019077.6; Issued May 7, 2025.
Malaysian IPO Office Action for corresponding MY Application No. PI 2023005227; Issued Jul. 16, 2025.
JPO Decision of Refusal for corresponding JP Application No. 2021-034495; issued Oct. 7, 2025.
KR Request for the Submission of an Opinion for corresponding KR Application No. 1020237029982; Issued Oct. 13, 2025.
SIPO Office Action for corresponding CN Application No. 202280019077.6; Issued Sep. 10, 2025.
IPO India Hearing Notice in reference to corresponding IN Application No. 202337061870 issued on Mar. 24, 2026.
MY Office Action issued for corresponding Malaysian Patent Application No. PI 2023005227; Issued Jul. 3, 2026.

* cited by examiner

FIG. 2

| | | COMPARATIVE EXAMPLE 1 | EXAMPLE 1 | EXAMPLES 2-8 |
|---|---|---|---|---|
| | ZEOLITE | Fe-Ga-Al-MFI | Fe-Ga-Al-MFI | Fe-Ga-Al-MFI |
| ACID DENSITY | (Si/(Fe + Ga + Al)) [mol/mol] | 91.5 | 91.5 | 91.5 |
| Fe MOLE COMPOSITION | (Fe/(Fe + Ga + Al)) [mol/mol] | 0.6 | 0.6 | 0.6 |
| Ga MOLE COMPOSITION | (Ga/(Fe + Ga + Al)) [mol/mol] | 0.1 | 0.1 | 0.1 |
| Al MOLE COMPOSITION | (Al/(Fe + Ga + Al)) [mol/mol] | 0.3 | 0.3 | 0.3 |
| | BINDER USED FOR MOLDING | $SiO_2$ (AE200) | $SiO_2$ (AE200) | $SiO_2$ (AE200) |
| ZEOLITE/BINDER MIXING RATIO | [wt%/wt%] | 65 / 35 | 65 / 35 | 65 / 35 |
| $P_2O_5$ CONTENT RATIO | [wt%] | 0.0 | 0.2 | 1.0 |

FIG. 3

| | COMPARATIVE EXAMPLE 1 | EXAMPLE 1 | EXAMPLE 2 | EXAMPLE 3 |
|---|---|---|---|---|
| CATALYST LOADING [mL] | 3.5 | 3.5 | 3.5 | 3.5 |
| HEIGHT OF CATALYST ZONE [mm] | 30 | 30 | 30 | 30 |
| INLET TEMPERATURE OF CATALYST ZONE [°C] | 648 | 650 | 653 | 652 |
| EXIT TEMPERATURE OF CATALYST ZONE [°C] | 649 | 650 | 651 | 649 |
| AVERAGE TEMPERATURE OF CATALYST ZONE [°C] | 649 | 649 | 648 | 650 |
| REACTION PRESSURE [MPa] | 0.15 | 0.15 | 0.15 | 0.15 |
| LHSV OF REACTION FEEDSTOCK [$h^{-1}$] | 6.0 | 6.0 | 6.0 | 6.0 |
| STEAM CHARGE [wt%] | 0.0 | 0.0 | 0.0 | 25.0 |
| ONE-PASS FEEDSTOCK CONVERSION RATE [wt%] | 71.5 | 75.5 | 79.9 | 70.8 |
| LOWER OLEFIN SELECTIVITY [wt%] | 51.0 | 50.3 | 49.4 | 58.2 |
| BTX SELECTIVITY [wt%] | 17.5 | 18.0 | 19.9 | 11.0 |

FIG. 6

| | | EXAMPLE 2 | EXAMPLE 4 | EXAMPLE 5 | EXAMPLE 6 | EXAMPLE 7 | EXAMPLE 8 |
|---|---|---|---|---|---|---|---|
| CATALYST LOADING | [mL] | 3.5 | 3.5 | 3.5 | 3.5 | 3.5 | 3.5 |
| HEIGHT OF CATALYST ZONE | [mm] | 30 | 30 | 30 | 30 | 30 | 30 |
| INLET TEMPERATURE OF CATALYST ZONE | [°C] | 653 | 624 | 614 | 599 | 588 | 564 |
| EXIT TEMPERATURE OF CATALYST ZONE | [°C] | 651 | 648 | 648 | 649 | 648 | 649 |
| AVERAGE TEMPERATURE OF CATALYST ZONE | [°C] | 648 | 631 | 627 | 621 | 616 | 607 |
| REACTION PRESSURE | [MPa] | 0.15 | 0.15 | 0.15 | 0.15 | 0.15 | 0.15 |
| LHSV OF REACTION FEEDSTOCK | [$h^{-1}$] | 6.0 | 6.0 | 6.0 | 6.0 | 6.0 | 6.0 |
| STEAM CHARGE | [wt%] | 0.0 | 0.0 | 0.0 | 0.0 | 0.0 | 0.0 |
| ONE-PASS FEEDSTOCK CONVERSION RATE | [wt%] | 79.9 | 77.4 | 78.8 | 77.8 | 78.0 | 79.3 |
| LOWER OLEFIN SELECTIVITY | [wt%] | 49.4 | 53.4 | 53.8 | 54.4 | 54.4 | 55.4 |
| BTX SELECTIVITY | [wt%] | 19.9 | 15.4 | 14.8 | 14.3 | 14.2 | 13.0 |

FIG. 7

| | | EXAMPLE 8 | EXAMPLE 9 | EXAMPLE 10 |
|---|---|---|---|---|
| ZEOLITE | | Fe-Ga-Al-MFI | Fe-Ga-Al-MFI | Fe-Ga-Al-MFI |
| ACID DENSITY | (Si/(Fe + Ga + Al)) [mol/mol] | 91.5 | 91.5 | 91.5 |
| Fe MOLE COMPOSITION | (Fe/(Fe + Ga + Al)) [mol/mol] | 0.6 | 0.6 | 0.6 |
| Ga MOLE COMPOSITION | (Ga/(Fe + Ga + Al)) [mol/mol] | 0.1 | 0.1 | 0.1 |
| Al MOLE COMPOSITION | (Al/(Fe + Ga + Al)) [mol/mol] | 0.3 | 0.3 | 0.3 |
| BINDER USED FOR MOLDING | | $SiO_2$ (AE200) | $SiO_2$ (AE380) | $SiO_2$ (HDK-T40) |
| BET SURFACE AREA OF BINDER | [$m^2$/g] | 200 | 380 | 387 |
| ZEOLITE/BINDER MIXING RATIO | [wt%/wt%] | 65 / 35 | 65 / 35 | 65 / 35 |
| $P_2O_5$ CONTENT RATIO | [wt%] | 1.0 | 1.0 | 1.0 |

FIG. 8

| | EXAMPLE 8 | EXAMPLE 9 | EXAMPLE 10 |
|---|---|---|---|
| CATALYST LOADING [mL] | 3.5 | 3.5 | 3.5 |
| HEIGHT OF CATALYST ZONE [mm] | 30 | 30 | 30 |
| INLET TEMPERATURE OF CATALYST ZONE [°C] | 564 | 564 | 565 |
| EXIT TEMPERATURE OF CATALYST ZONE [°C] | 649 | 650 | 648 |
| AVERAGE TEMPERATURE OF CATALYST ZONE [°C] | 607 | 604 | 606 |
| REACTION PRESSURE [MPa] | 0.15 | 0.15 | 0.15 |
| LHSV OF REACTION FEEDSTOCK [$h^{-1}$] | 6.0 | 6.0 | 6.0 |
| STEAM CHARGE [wt%] | 0.0 | 0.0 | 0.0 |
| ONE-PASS FEEDSTOCK CONVERSION RATE [wt%] | 79.3 | 83.2 | 83.9 |
| LOWER OLEFIN SELECTIVITY [wt%] | 55.4 | 55.0 | 53.2 |
| BTX SELECTIVITY [wt%] | 13.0 | 13.5 | 16.0 |

COMPOSITE CATALYST, METHOD FOR PRODUCING COMPOSITE CATALYST, AND METHOD FOR PRODUCING LOWER OLEFINS

CROSS REFERENCE TO RELATED APPLICATIONS

This application is a continuation under 35 U.S.C. § 120 of PCT/JP2022/007338, filed Feb. 22, 2022, which is incorporated herein by reference, and which claimed priority to Japanese Application No. 2021-034495, filed Mar. 4, 2021. The present application likewise claims priority under 35 U.S.C. § 119 to Japanese Application No. 2021-034495, filed Mar. 4, 2021, the entire content of which is also incorporated herein by reference.

BACKGROUND OF THE INVENTION

1. Field of the Invention

The present disclosure relates to a composite catalyst, a method for producing a composite catalyst, and a method for producing lower olefins.

2. Description of the Related Art

Lower olefins, such as ethylene and propylene, are important basic feedstocks in petrochemistry and demands for them presumably keep steady growth also in future. At present, 50% or more of propylene is produced by steam cracking (with a steam cracker) typically from naphtha. The technology is, however, a highly energy-consuming process requiring temperature as high as 800 to 900° C. and excessive charge of steam for decomposition, due to its non-catalytic nature.

In addition, the technology yields ethylene as a main product and propylene as a by-product, with a fixed ratio of production of ethylene/propylene nearly at 2/1, when started from naphtha. This raises a concern that the propylene production would not be able to keep up with expanding demand in future. From this point of view, there is a strong desire for an alternative process which can efficiently produce propylene from naphtha, with a minimum energy consumption.

As an alternative to the steam cracker, research and development have been made at present on an energy-saving method for producing propylene, to which a fixed bed catalytic cracking of naphtha with use of a zeolite-based catalyst is applied. For example, proposals have been made on use of a crystalline aluminosilicate that has an MFI-type structure, and contains iron but no gallium, or contains iron and gallium, as a catalyst for producing lower olefins from a low-boiling hydrocarbon feedstock such as light naphtha (see, Patent Literatures 1 to 3, for example). With the zeolite catalyst described in Patent Literatures 1 to 3, it now becomes possible to produce propylene which amounts more than ethylene, at a relatively low reaction temperature, and to extend the service life of catalyst.

Patent Literature 1 JP 2014-24005 A

Patent Literature 2 JP 2014-24006 A

Patent Literature 3 JP 2014-24007 A

For implementation of production of lower olefins with use of a zeolite catalyst, a fixed bed system needing a lower equipment cost will be preferred over a fluidized bed system. In this case, the zeolite catalyst arranged in a fixed manner is expected to stably and continuously produce the lower olefins over a long period, which raises a need for further extending the service life of zeolite catalyst. For further reduction of the production cost aimed at the implementation, the zeolite catalyst is further expected to have not only long service life, but also capability of producing the lower olefins with a high conversion rate and high selectivity.

SUMMARY OF THE INVENTION

Considering the above circumstances, it is therefore a general purpose of the present disclosure to provide a composite catalyst that excels both in conversion rate and lower olefin selectivity, in production of the lower olefins from the hydrocarbon feedstock.

One embodiment of the present disclosure relates to a composite catalyst. The composite catalyst contains a zeolite which is a crystalline aluminosilicate that contains gallium and iron and has a skeletal structure of an 8- to 12-membered ring; or a zeolite which is a crystalline aluminosilicate that contains iron but no gallium and has a skeletal structure of an 8- to 12-membered ring; silicon dioxide as a binder; and diphosphorus pentoxide.

Another embodiment of the present disclosure relates to a method for producing the composite catalyst. The production method includes a hydrothermal synthesis step, a molding step, an ion exchange step, and a phosphorus modification step.

Still another embodiment of the present disclosure relates to a method for producing lower olefins. The production method includes feeding a hydrocarbon feedstock to an inlet of a catalyst zone that contains the aforementioned composite catalyst, and obtaining lower olefins from an exit of the catalyst zone, while setting a temperature difference between at the inlet and at the exit to 20° C. to 150° C.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 2 is a chart summarizing chemical composition of the individual composite catalysts of Examples 1 to 8 and Comparative Example 1.

FIG. 3 is a chart that summarizing results of the performance evaluation test of the individual composite catalysts of Examples 1 to 3 and Comparative Example 1.

FIG. 6 is a chart summarizing results of the performance evaluation test of the individual composite catalysts of Examples 2, 4 to 8.

FIG. 7 is a chart summarizing chemical composition of the individual composite catalysts of Examples 8 to 10.

FIG. 8 is a chart summarizing results of the performance evaluation test of the individual composite catalysts of Examples 8 to 10.

DETAILED DESCRIPTION OF THE INVENTION

Figure 1:
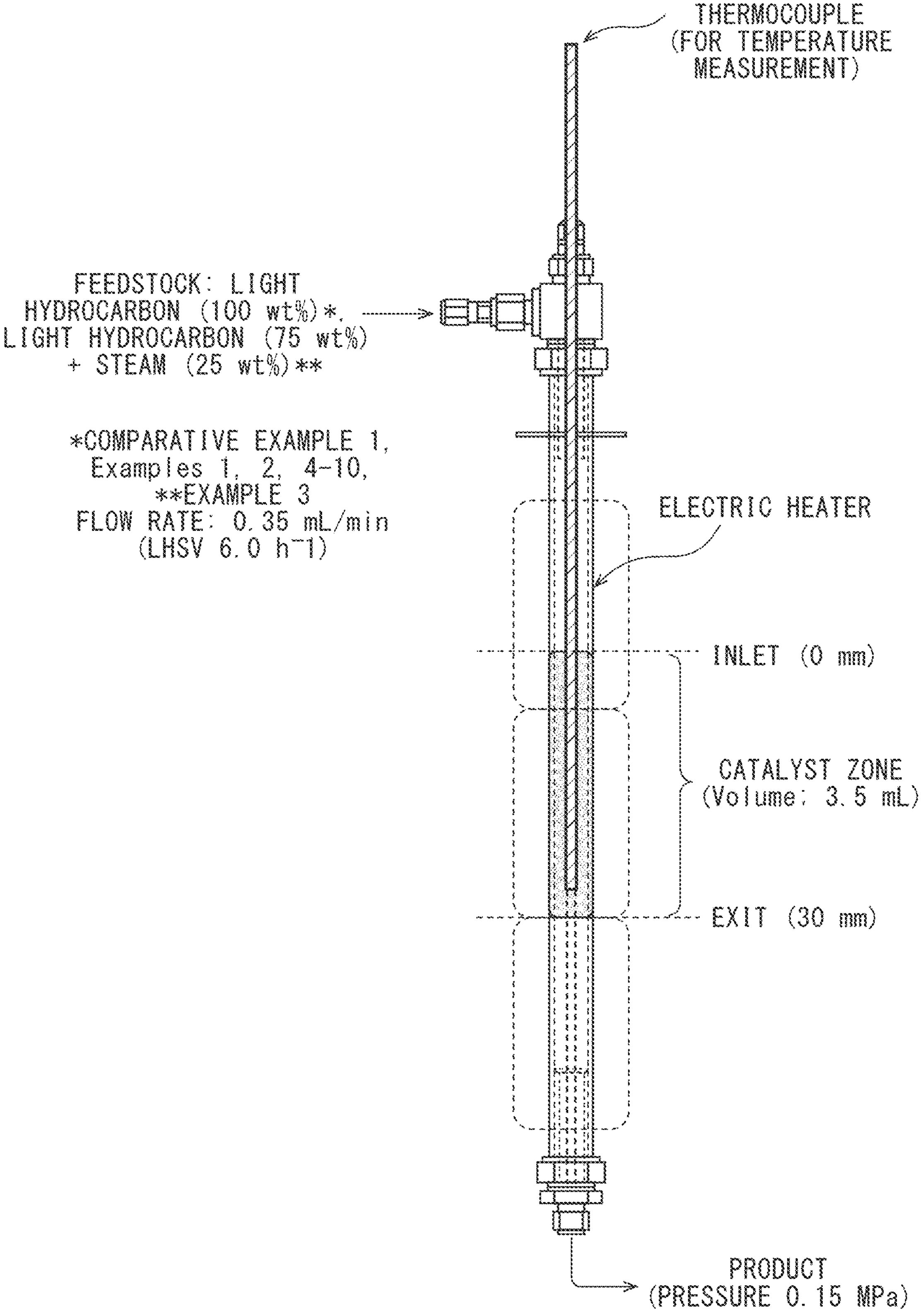
FIG. 1 is a schematic drawing of a reactor used in a performance evaluation test of the individual composite catalysts of Examples 1 to 10 and Comparative Example 1.

The invention will now be described by reference to the preferred embodiments. This does not intend to limit the scope of the present invention, but to exemplify the invention.

Composite Catalyst

The composite catalyst of the present disclosure is intended for use in production of lower olefins from a hydrocarbon feedstock and contains a zeolite which is a crystalline aluminosilicate that contains gallium and iron, or iron only, and has a skeletal structure having 8- to 12-membered ring; silicon dioxide; and diphosphorus pentoxide. With such structure in which a catalytic zeolite, silicon dioxide as a binder, and diphosphorus pentoxide are combined, it now becomes possible to increase the conversion rate of the hydrocarbon feedstock, while suppressing the selectivity between ethylene and propylene from degrading.

Although aluminum oxide (alumina powder) has been used as a binder in Patent Literatures 1 to 3, the present inventors found that use of silicon dioxide (silica) as a binder obviously extended the service life of the catalyst. That is, the present inventors found that silicon dioxide mixed into the aforementioned zeolite extended the service life of the catalyst. This is presumably due to influence of silicon dioxide that coexists at least at a part of acid sites that reside on the outer face of zeolite. For example, declined acid strength at the acid sites presumably suppresses any aromatic hydrocarbon from generating from the lower olefins on the outer face of zeolite, and this possibly inhibits coke, which is causative of shortening of the service life of catalyst, from generating. Furthermore, inclusion of diphosphorus pentoxide into the catalyst can increase the conversion rate of the hydrocarbon feedstock. This enables production of lower olefins from the hydrocarbon feedstock in a fixed bed system capable of producing the lower olefins in a sufficiently efficient manner over a long period.

The zeolite, which is a crystalline aluminosilicate, has a skeletal structure of an 8-12-membered ring. Each skeletal structure of zeolite is compiled into a database by the International Zeolite Association, to which a framework type code consisting of three capital letters is assigned. This framework type code specifies only the geometry of the skeleton.

For example, the framework type codes for the skeletal structure of 8-membered ring include LTA; the framework type codes for the skeletal structure of 10-membered ring include FER, MWW, and MFI; and the framework type codes for the skeletal structure of 12-membered ring include MOR, LTL, FAU, and BEA. The description above enumerated only parts of the framework type codes for zeolite having each number of ring members. Zeolite will have the pore size affected by the number of ring members in the skeletal structure, so that those having an 8- to 12-membered ring will have the pore size within a certain range. For example, zeolite as a whole has a pore size of about 0.2 to 1.0 nm, and zeolite having a representative skeletal structure with an 8- to 12-membered ring has a pore size of about 0.40 nm to 0.75 nm. In the present embodiment, the pore size of zeolite is preferably such as making the zeolite suitably applicable to production of propylene or ethylene making use of the catalytic function thereof, typically from C4 to C8 lower olefins as the hydrocarbon feedstock and is preferably within the aforementioned range from 0.40 nm to 0.75 nm for example but is not limited thereto.

In this case, the number of ring members in the skeletal structure of zeolite is preferably 8 to 12 as described above and is more preferably 10 to 12. For example, known MFI-type zeolite having 10-membered ring structure includes ZSM-5 (Zeolite Socony Mobil-5), and known BEA-type zeolite having 12-membered ring structure include beta zeolite. MFI-type zeolite and beta zeolite are suitably applicable as the zeolite with 8- to 12-membered ring. In particular, MFI-type zeolite is suitably used.

Zeolite used in the present embodiment is typically defined to be crystalline aluminosilicate that contains no gallium (Ga) element but contains iron (Fe) element, or crystalline aluminosilicate that contains gallium (Ga) element and iron element. Fe functions to suppress acid strength of the acid site in zeolite. Meanwhile, Ga functions to promote dehydrogenation reaction of alkane. The zeolite catalyst of the present embodiment is a composite catalyst obtainable by molding and calcining together with a binder, followed by phosphorus modification, wherein silicon dioxide is used as the binder.

The composite catalyst of the present embodiment preferably has a diphosphorus pentoxide content of 0.1 to 5.0 wt %, more preferably 0.1 to 3.0 wt %. With the diphosphorus pentoxide content fallen within these ranges, the catalyst can further improve the conversion rate of the hydrocarbon feedstock.

Zeolite, when composed of an iron-containing but gallium-free MFI-type crystalline aluminosilicate, preferably has a molar ratio of iron element (iron element/(iron element+aluminum element (Al))) of 0.4 to 0.7, more preferably 0.4 to 0.6.

Zeolite, when composed of an iron-containing but gallium-free MFI-type crystalline aluminosilicate, preferably has an acid density (element ratio given by silicon element (Si)/(iron element+aluminum element)) of 75.0 to 200.0, more preferably 80.0 to 200.0. Note that the element ratio is a compositional ratio based on the number of moles of the individual elements described above.

Zeolite, when composed of an iron-and-gallium-containing MFI-type crystalline aluminosilicate, preferably has a molar ratio of iron element (iron element/(iron element+gallium element+aluminum element)) of 0.2 to 0.6, more preferably 0.3 to 0.5.

Zeolite, when composed of an iron-and-gallium-containing MFI-type crystalline aluminosilicate, preferably has a molar ratio of gallium element (gallium element/(iron element+gallium element+aluminum element)) of 0.1 to 0.4, more preferably 0.2 to 0.4.

Zeolite catalyst, when composed of an iron-and-gallium-containing MFI-type, preferably has an acid density (element ratio given by silicon element/(iron element+gallium element+aluminum element)) of 75.0 to 200.0, more preferably 80.0 to 200.0.

With use of the aforementioned zeolite of this embodiment, which is an MFI-type crystalline aluminosilicate that contains iron element, it now becomes possible to control the acid strength on the basis of the iron element content and the acid density, and addition of gallium can further enhance the promoting action for dehydrogenation of alkane. The alkane may be catalytically decomposed at the acid site of zeolite, where a carbon-carbon double bond generates to produce lower olefins. If the acid strength at the acid site is too large, the produced lower olefins will not leave the acid site but will further be reacted to cause cyclization and dehydrogenation to produce aromatic hydrocarbon. Increased amount of production of the aromatic hydrocarbon will increase the amount of deposition of coke, thereby shortening the service life of the composite catalyst. It is, therefore, important to control the acid strength, in order to reduce the amount of coke deposition.

With the molar ratio of iron element, the molar ratio of gallium element, and the acid density controlled within the aforementioned ranges, the catalyst can further improve the yield of propylene, and can further suppress the generation of aromatic carbon responsible for coke generation.

In the composite catalyst according to the present embodiment, the zeolite is a crystalline aluminosilicate that contains iron but no gallium, and preferably has an acid density, which is defined as a molar ratio of silicon relative to the sum of iron and aluminum, of 75.0 to 200.0, and a molar ratio of iron, relative to the sum of iron and aluminum, of 0.4 to 0.7. With such structure having the acid density and the molar ratio of iron controlled within the aforementioned ranges, the catalyst can further increase the amount of production of propylene relative to ethylene and can further enhance a suppressive effect over the production of aromatic hydrocarbon, in the coexistence of silicon dioxide as a binder.

In the composite catalyst according to the present embodiment, the zeolite is a crystalline aluminosilicate that contains iron and gallium, and preferably has an acid density, which is defined as a molar ratio of silicon relative to the sum of iron, gallium, and aluminum, of 75.0 to 200.0, has a molar ratio of gallium relative to the sum of iron, gallium, and aluminum, of 0.1 to 0.4, and has a molar ratio of iron relative to the sum of iron, gallium, and aluminum, of 0.2 to 0.6. With such structure having the acid density, the molar ratio of iron (Fe), and the molar ratio of gallium (Ga) controlled within the aforementioned ranges, the catalyst can further increase the amount of production of propylene relative to ethylene, and can suppress the production of aromatic hydrocarbon, in the coexistence of silicon dioxide as a binder. Here, iron functions to suppress the acid strength at the acid site in zeolite, meanwhile gallium functions to promote a dehydrogenation reaction of alkane.

The composite catalyst of the present embodiment preferably has a silicon dioxide (silica) content of 5 to 50 wt %, more preferably 5 to 40 wt %. With the content of silicon dioxide controlled within these ranges, the catalyst can more effectively reduce the amount of production of aromatic hydrocarbon, while suppressing the amount of production of propylene from decreasing. This can more effectively extend the service life of zeolite in the composite catalyst. Reduction in the silicon dioxide content and increase in the zeolite content are preferred from the viewpoint of increasing the yield of lower olefins, meanwhile increase in the silicon dioxide content is preferred from the view point of suppressing the generation of aromatic hydrocarbon. Furthermore, silicon dioxide as a binder presumably has an action of covering and deactivating the acid sites on the outer surface of zeolite, stronger than that of aluminum oxide (alumina) as a binder.

The silicon dioxide preferably has a BET specific surface area of 50 to 500 $m^2/g$, more preferably 100 to 400 $m^2/g$. With the BET specific surface area controlled within these ranges, the feedstock conversion can be further improved while maintaining a high level of lower olefin selectivity.

Method for Producing Composite Catalyst

The composite catalyst according to the aforementioned embodiment may be produced by following the four steps below: 1. hydrothermal synthesis step; 2. molding step; 3. ion exchange step; and 4. phosphorus modification step. The individual steps will be explained below.

1. Hydrothermal Synthesis Step

"Hydrothermal synthesis method" is a general term for methods for synthesizing substances in the presence of water at high temperature and high pressure. Many zeolites in the form of crystalline aluminosilicates are synthesized by the hydrothermal synthesis method. Feedstocks widely used in the synthesis include silica sources, such as sodium silicate, colloidal silica, and fumed silica; alumina sources, such as aluminum hydroxide and sodium aluminate; structure-directing agents, such as amine; mineralizers, such as alkali metal hydroxide; and water.

In the present embodiment, an iron source, such as, for example, iron nitrate, iron oxide, iron sulfate, iron phosphate, iron chloride, iron bromide, metal iron (iron powder) or iron organic acid, is added to the feedstock. When producing a composite catalyst that contains iron and gallium, the feedstock will have a gallium source, such as, for example, gallium nitrate, gallium oxide, gallium sulfate, gallium phosphate, gallium chloride, gallium bromide or gallium hydroxide, added thereto, in addition to the iron source. These components are mixed to prepare a highly reactive amorphous hydrogel (mother gel), the mixture is charged in an autoclave, which is a pressure-resistant reactor, and is then heated at about 150° C. for a predetermined duration of time, to synthesize the zeolite. After the hydrothermal synthesis reaction, the product is subjected to steps including isolation, water washing, drying, and calcining (for decomposing and removing the structure-directing agent), to obtain a powdery zeolite.

The method for producing zeolite will further be detailed. A mother gel A that contains colloidal silica having a particle size of 8 to 11 nm as a fine silica which is a silicon source, and sodium hydroxide (NaOH) for pH adjustment; and a mother gel B that contains $Al_2(SO_4)$-$nH_2O$ as an aluminum source, $Ga(NO_3)_3$-$nH_2O$ as a gallium source, $Fe(NO_3)_3$-$nEH_2O$ as an iron source, and tetrapropylammonium bromide (TPrABr) as a structure-directing agent, are prepared. In addition, the amount of addition of TPrABr, as the structure-directing agent, is preferably reduced.

Next, the mother gel A and the mother gel B are mixed under stirring (for example, for 15 minutes). A highly reactive amorphous hydrogel is thus prepared. The mother gels, thus mixed under stirring, are then aged (at 60° C. overnight, for example). The aforementioned hydrothermal synthesis is then conducted, while stirring the mixture at 110° C. to 200° C., at a rotation speed of 150 rpm to 1000 rpm (hydrothermal synthesis proceeds typically in an autoclave under the self-controlled pressure). That is, the hydrogel is crystallized under high temperature and high pressure. The reaction temperature is however relatively low, aiming at suppressing production of coarse particle, by nucleus growth under such low temperature. The stirring speed is relatively high, aiming at increasing the amount of nucleus generation. The hydrogel is stirred for 24 hours for example under such conditions, to obtain a crystal. The obtained crystal is washed with water, and then dehydrated by centrifugation. The crystal is then dried typically at 120° C. for 3 hours, and calcined at 550° C. for 3 hours, to remove TPrABr. Note that in a gallium-free preparation, the gallium source is not added to the mother gel B.

2. Molding Step

In general, zeolite intended for industrial use as a catalyst is often molded typically into a cylindrical shape, from the viewpoint of improving the mechanical property and reducing pressure loss. This step mainly includes steps typically for kneading the zeolite mainly synthesized as described above with a silicon dioxide as a binder, molding, drying, and calcining. The molding step typically relies upon extrusion molding.

For example, the powdery zeolite obtained through the aforementioned hydrothermal synthesis step, or the ion exchange step, is mixed with silica powder, and with starch as a molding aid, to which an aqueous sodium hydroxide solution (aqueous alkaline solution) is added, and the mixture is kneaded to obtain a lumpy mixture. Note that the molding aid is not limited to starch and may only be a substance for example that increases the viscosity upon addition of water, that can make a mixture of zeolite powder kneaded with silica powder and water formed into a lump, that can be almost completely converted by calcining into water and carbon dioxide and can disappear from a molded article. For example, polyvinyl pyrrolidone (PVP) may be used. The mixture is processed into a cylindrical shape typically by extrusion molding and dried at 120° C. for about 3 hours. Next, the product is calcined at 550° C. for 3 hours under air circulation, to obtain a molded article.

When molding the mixture of zeolite and silicon dioxide, the molding step preferably uses an aqueous alkaline solution that contains starch as a molding aid. With the aqueous alkaline solution that contains starch thus added to zeolite and silicon dioxide during kneading so as to create thickening property, the mixture will be more easily processed into a lumpy mixture.

The ion exchange step may be followed by the molding step, or the molding step may be followed by the ion exchange step. It is preferred that the molding step is followed by the ion exchange step.

3. Ion Exchange Step

Many of chemical reactions that employ zeolite as a catalyst make use of a property of zeolite as a solid acid, wherein such acidic property develops upon introduction of an OH— group (Brønsted acid site) into the zeolite. Such acid property is developed, typically by applying an ion exchange reaction. Many of the zeolite obtained by the hydrothermal synthesis contains sodium cation ($Na^+$) for balancing the charge, which is replaced with proton ($H^+$) by ion exchange. Note that the zeolite may alternatively be ion-exchanged once with ammonium ion ($NH_4^+$) with use of an $NH_4NO_3$ solution, and then subjected to drying and calcining to remove ammonia, thereby exchanging the ion further with proton ($H^+$). For example, the proton-type zeolite catalyst is obtainable by a set of ion exchange with an aqueous ammonium nitrate solution under boiling reflux and subsequent water washing, which is repeated four times, followed by drying at 120° C. for 3 hours, and calcining at 550° C. for 3 hours under air circulation.

In a case where the molding step is followed by the ion exchange step, the composite catalyst finally obtainable after the phosphorus modification, when applied to production of the lower olefins, may possibly suppress production of aromatic hydrocarbon responsible for coke generation. In addition, the molded zeolite catalyst obtained after the molding step is easier to handle than the powdery crystalline aluminosilicate obtained in the hydrothermal synthesis step and can therefore improve the workability in the ion exchange step.

4. Phosphorus Modification Step

After completion of the molding step and the ion exchange step, the obtained zeolite catalyst is impregnated with an aqueous phosphorus precursor solution, dried, and calcined to be modified with phosphorus. By this phosphorus modification step, a composite catalyst that contains diphosphorus pentoxide is obtained (also referred to as phosphorus-modified composite catalyst, hereinafter). The phosphorus precursors are exemplified by diammonium hydrogen phosphate ($(NH_4)_2HPO_4$), and phosphoric acid ($H_3PO_4$). Reaction conditions for the phosphorus modification step may be properly determined by those skilled in the art. For example, the composite catalyst is impregnated with an aqueous phosphorus precursor solution for 5 minutes under boiling reflux. Thereafter, the product is washed with purified water, dried, and calcined at 550° C. for 3 hours under air circulation, to obtain the phosphorus modified composite catalyst.

Although production of the composite catalyst may rely upon the ion exchange step and the molding step conducted in this order, it is preferred to conduct the hydrothermal synthesis step, the molding step, the ion exchange step, and the phosphorus modification step in this order. The ion exchange step will enjoy improved workability when directed to the composite catalyst formed into a predetermined shape, rather than to the powdery zeolite obtained in the hydrothermal synthesis. In addition, generation of the aromatic hydrocarbon would be more effectively suppressed, by molding the composite catalyst with use of silicon dioxide as the binder, and then by creating the acid site by the ion exchange step.

Method for Producing Lower Olefins

The method for producing lower olefins includes feeding a hydrocarbon feedstock to an inlet of a catalyst zone that contains the composite catalyst according to this embodiment and obtaining the lower olefins from an exit of the catalyst zone, while setting a temperature difference of 20° C. to 150° C. between the inlet and the exit. Such structure can suppress the generation of the aromatic hydrocarbon and can increase the amount of production of the lower olefins. That is, the lower olefin selectivity may be increased.

In this embodiment, for example, the catalyst zone that contains the aforementioned composite catalyst is arranged as a fixed bed in a reactor. The hydrocarbon feedstock fed into the reactor is allowed to pass through the catalyst zone while keeping the contact therewith. This converts the hydrocarbon feedstock into the lower olefins such as ethylene and propylene. The thus produced lower olefins are obtainable from the exit of the catalyst zone. When allowing the hydrocarbon feedstock to pass through the catalyst zone, the temperature difference between the inlet and the exit of the catalyst zone is set to 10 to 200° C., preferably 20 to 100° C. Such temperature difference can suppress the generation of the aromatic hydrocarbon and can enhance the lower olefin selectivity.

The contact reaction between the hydrocarbon feedstock and the catalyst zone can proceed in a mild temperature range of 530° C. to 650° C., more preferably 550° C. to 640° C. This level of temperature, lower than that in steam cracking, excels in energy efficiency, and can save the cost. Production of the lower olefins at relatively low temperatures can also suppress the generation of the aromatic hydrocarbon, thereby extending the service life of the composite catalyst.

Although workable in this embodiment for a long period of time, the composite catalyst would degrade with time, moderately decreasing the amount of production of the lower olefins. Now typically by gradually elevating, with time, the contact temperature between the hydrocarbon feedstock and the catalyst zone, the amount of production of the lower olefins may be stabilized over a long period, and the timing for replacement or regeneration of the composite catalyst may be delayed.

When feeding the hydrocarbon feedstock in the form of gas to the catalyst zone, the gas to be fed preferably contains 15 wt % or more, and more preferably 50 wt % or more, of the hydrocarbon feedstock. The contact time of the hydrocarbon feedstock with the catalyst zone is preferably 0.08 to 1.0 h, and more preferably 0.08 to 0.4 h. With the contact time controlled in these ranges, it now becomes possible to produce the lower olefins more efficiently, and to extend the service life of the composite catalyst, while suppressing the amount of production of the aromatic hydrocarbon. That is, shortened contact time would reduce the amount of production of the lower olefins, but will concomitantly reduce the amount of production of the aromatic hydrocarbon, thus extending the service life of the composite catalyst. Meanwhile, extended contact time will increase the amount of production of the lower olefins but would concomitantly increase the amount of production of the aromatic hydrocarbon, thus shortening the service life of the composite catalyst. It is therefore preferred to determine the contact time, in consideration of the amount of production of the lower olefins and the service life of the composite catalyst.

In an exemplary case where a feedstock gas such as light naphtha is used as the hydrocarbon feedstock, the feedstock gas is fed to the reactor without being diluted with a diluent such as an inert gas, e.g., nitrogen, or water vapor. That is, the hydrocarbon feedstock is brought into contact with the composite catalyst to react therewith. The feedstock gas may contain a diluent. In this case, the gas to be fed to the composite catalyst preferably contains 15 wt % or more of the hydrocarbon feedstock such as light naphtha, wherein the content is more preferably 50 wt % or more. A possible method is such as arranging the aforementioned composite catalyst as a fixed bed in the reactor and allowing the feedstock gas to be fed into the reactor to pass therethrough, while keeping contact with the composite catalyst. The reaction in this case is allowed to proceed in a mild temperature range from 530° C. to 650° C., more preferably 550° C. to 640° C., to produce ethylene and propylene.

The hydrocarbon feedstock is typically a low-boiling-point hydrocarbon feedstock, such as light naphtha. Naphtha (full-range naphtha) is a range of products obtainable by fractional distillation of crude oil with use of a normal pressure distillation apparatus, and having the boiling point approximately within the range from 30 to 200° C. Among the ranges of naphtha, those having the boiling point within the range from approximately 30 to 100° C. is referred to as light naphtha, and those having the boiling point within the range from approximately 100 to 200° C. is referred to as heavy naphtha. The light naphtha corresponds to a fraction mainly composed of C5 pentane and C6 hexane.

The low-boiling-point hydrocarbon feedstock, although being basically the light naphtha, may partially contain heavy naphtha, or may be the full-range naphtha. Alternatively, the low-boiling hydrocarbon feedstock may be other than naphtha, to which typically applicable is any of fractions which are basically equivalent to the light naphtha, and composed of natural gas or other hydrocarbon feedstock, but other than petroleum. Also, by-product and the like that occurs when producing various products from petroleum or natural gas may be used as the hydrocarbon feedstock, to which hydrocarbon having a boiling point not so high is applicable in principle. The lower olefins in this embodiment may occasionally be defined to include olefins having a less number of carbon atoms, such as ethylene, propylene, butene, or olefins having larger numbers of carbon atoms, for example, C5, C8, etc. The lower olefins herein include at least C2 ethylene and C3 propylene.

In the reaction for producing the lower olefins, the contact time, defined as the reciprocal of liquid hourly space velocity (LHSV) of the hydrocarbon feedstock, is preferably 0.08 to 1.0 h, and more preferably 0.08 to 0.4 h. The LHSV is preferably 1.0 to 12.5 h-1, and more preferably 2.5 to 12.5 h-1. Now, the LHSV is defined as the rate at which the hydrocarbon feedstock in the liquid form is fed to the catalyst zone, and the contact time is defined as the time during which the hydrocarbon feedstock in the liquid form passes through the catalyst zone. Although the feedstock when fed to the catalyst zone has been gasified from the liquid state as described above, the discussion herein employs the hourly space velocity of the feedstock to be fed to the reactor, in the form of liquid before being gasified. Note that the space velocity applicable here may alternatively be gas hourly space velocity (GHSV) of the feedstock gas or may be weight hourly space velocity (WHSV).

In the production of lower olefins, the higher the reaction temperature, the larger the conversion rate of the hydrocarbon feedstock will be, the larger the amount of production of the lower olefins, and the larger the amount of production of aromatic hydrocarbon will be. It is therefore necessary to determine the reaction temperature while balancing the energy efficiency during heating, the amount of production of the lower olefins, and the service life of the composite catalyst affected by increase of the aromatic hydrocarbon. With the reaction temperature controlled within the aforementioned range, it now becomes possible to keep a long service life of the composite catalyst, and to keep stable production of the lower olefins.

In the production of lower olefins, the longer the contact time, the larger the conversion rate of the hydrocarbon feedstock will be, the larger the amount of production of the lower olefins, and the larger the amount of production of aromatic hydrocarbon will be. It is therefore necessary to determine the contact time while balancing the amount of production of the lower olefins, and the service life of the composite catalyst affected by increase of the aromatic hydrocarbon. With the contact time controlled within the aforementioned range, it now becomes possible to keep a long service life of the composite catalyst, and to keep stable production of the lower olefins.

Now, the composite catalyst of this embodiment, when used in a continuous manner, will enjoy longer service life, since the amount of production of aromatic hydrocarbon is smaller than before, and thus the amount of carbon deposition is small. In the production of the lower olefins over a long duration of time, the yield of the lower olefins will gradually decrease with time, if the composite catalyst is scheduled to be replaced or regenerated after the yield of the lower olefins dropped down to the preset lower limit. Now, the yield of the lower olefins may be stabilized over a long duration, by elevating the reaction temperature or by increasing the contact time, i.e., slowing down the space velocity (LHSV), according to the lapse of time, so as to suppress the yield of the lower olefins from decreasing.

Although such elevation of the reaction temperature and slowdown of the space velocity would increase the amount of production of the aromatic hydrocarbon, again the amount of production of aromatic hydrocarbon will decrease with time. Hence, a decreasing tendency of the amount of production of aromatic hydrocarbon will not largely vary with time, even if the reaction temperature would elevate or the space velocity would decrease, thus making the aromatic hydrocarbon less likely to increase. Note that elevation of the reaction temperature and the slowdown of the space velocity, i.e., increase of contact time, of feedstock, according to the lapse of time, may take place independently, or may be combined. In a case where the elevation of the reaction temperature and the slowdown of the space velocity are combined, such increase in the reaction temperature and the slowdown of the space velocity may occur at the same time, or at different times. For example, during continuous production, the space velocity may be slowed down in the early stage and the reaction temperature may be elevated in the later stage, or vice versa. Alternatively, elevation of the reaction temperature and slowing down of the space velocity may be alternated, or, the elevation of the reaction temperature and the slowing down of the space velocity may take place at different frequencies, such that the space velocity is slowed down once for every three times of elevation of the reaction temperature.

In the composite catalyst, the method for producing the composite catalyst, and the method for producing lower olefins according to the aforementioned embodiment use silica as the binder for molding the powdery zeolite, and also use diphosphorus pentoxide, thereby making it possible to suppress coke generation, and to increase the conversion rate while maintaining a high level of lower olefin selectivity. Hence, in the production of the lower olefins with use of the composite catalyst, the lower olefins may be produced efficiently, and continuously over a period as long as of 1000 hours or longer, within a mild temperature range from approximately 530 to 650° C., which is regarded as a low temperature range, in the field of production of lower olefins.

EXAMPLES

Next, Examples of the present disclosure will be explained. These Examples by no means limit the present disclosure.

Example 1

Method for Synthetizing Fe—Ga—Al-MFI Zeolite

A solution containing 58.9 g of colloidal silica ($SiO_2$ 30.6 wt %, $Na_2O$ 0.4 wt %, $H_2O$ 69.0 wt %) and 2.26 g of sodium hydroxide was prepared as solution A, and a solution containing 0.19 g of aluminum sulfate n-hydrate, 0.11 g of gallium nitrate n-hydrate, 0.24 g of iron nitrate nonahydrate, 3.10 g of tetrapropylammonium bromide and 187.8 g of purified water was prepared as solution B. The solution A and the solution B were gradually mixed under stirring at room temperature, and then vigorously stirred in a mixer for 15 minutes. The mixed solution was kept at 60° C. and allowed to stand still overnight, and then subjected to a hydrothermal synthesis reaction in an autoclave with self-controlled pressure, under conditions of 115° C., 72 hours, and 900 rpm. After cooled, the product was washed thoroughly with purified water. The product was then dried at 120° C. for 3 hours, followed by calcining at 550° C. for 3 hours under air circulation, to synthesize a powdery Na-type MFI zeolite that contains Fe, Ga, and Al (denoted as Fe—Ga—Al-MFI zeolite, hereinafter). The zeolite was found, by X-ray fluorescence analysis, to have molar composition ratios of elements represented by Si/(Fe+Ga+Al) =91.5, Fe/(Fe+Ga+Al)=0.6, Ga/(Fe+Ga+Al)=0.1, and Al/(Fe+Ga+Al)=0.3 (see FIG. 2).

Method for Preparing Fe—Ga—Al-MFI/AE200 Catalyst

Predetermined amounts of the powdery Na-type Fe—Ga—Al-MFI zeolite synthesized according to the aforementioned procedures, a silica powder (AEROSIL (registered trademark) 200, from Nippon Aerosil Co., Ltd., BET specific surface area: 200 $m^2/g$) as a binder, and a starch as a molding aid were mixed, and the mixture was then kneaded while adding an appropriate amount of an aqueous sodium hydroxide solution (NaOH concentration: 4.5 wt %), to obtain a lumpy zeolite/silica mixture. The mixture was then molded into cylinders (1.0 mm diameter) through an extrusion molding machine, dried at 120° C. for 3 hours, and calcined at 550° C. for 3 hours under air circulation, to obtain a Fe—Ga—Al-MFI zeolite/silica composite. The composite was subjected to ion exchange with a 2.2 mol/L aqueous ammonium nitrate solution under boiling reflux and subsequent water washing, which were cycled four times (with an ion exchange time per cycle of 2 hours, and with the 2.2 mol/L aqueous ammonium nitrate solution refreshed for each cycle), dried at 120° C. for 3 hours, and calcined at 550° C. for 3 hours under air circulation, to prepare a proton-type Fe—Ga—Al-MFI zeolite/silica composite catalyst (referred to as Fe—Ga—Al-MFI/AE 200 catalyst, hereinafter). The catalyst was found, by X-ray fluorescence analysis, to have a weight composition represented by Fe—Ga—Al-MFI/AE200=65/35 [wt %/wt %] (see FIG. 2).

Method for Preparing P(0.2)-Fe—Ga—Al-MFI/AE200 Catalyst ($P_2O_5$ Loading: 0.2 wt %)

The cylindrical Fe—Ga—Al-MFI/AE200 catalyst prepared according to the aforementioned procedures was impregnated with a 0.5 mol/L aqueous diammonium hydrogen phosphate solution under boiling reflux for 5 minutes, the heating was stopped, and the product was allowed to stand still overnight for natural cooling. The product was washed with a sufficient amount of purified water, dried at 120° C. for 3 hours, and calcined at 550° C. for 3 hours under air circulation, to prepare a phosphorus-modified Fe—Ga—Al-MFI/AE200 catalyst (referred to as P(0.2)-Fe—Ga—Al-MFI/AE200 catalyst, hereinafter). The loading (weight composition) of the phosphorus compound was found, by fluorescent X-ray analysis, to be 0.2 wt % in terms of diphosphorus pentoxide ($P_2O_5$) (see FIG. 2).

Method for Performance Evaluation Test of P(0.2)-Fe—Ga—Al-MFI/AE200 Catalyst

Figure 4:
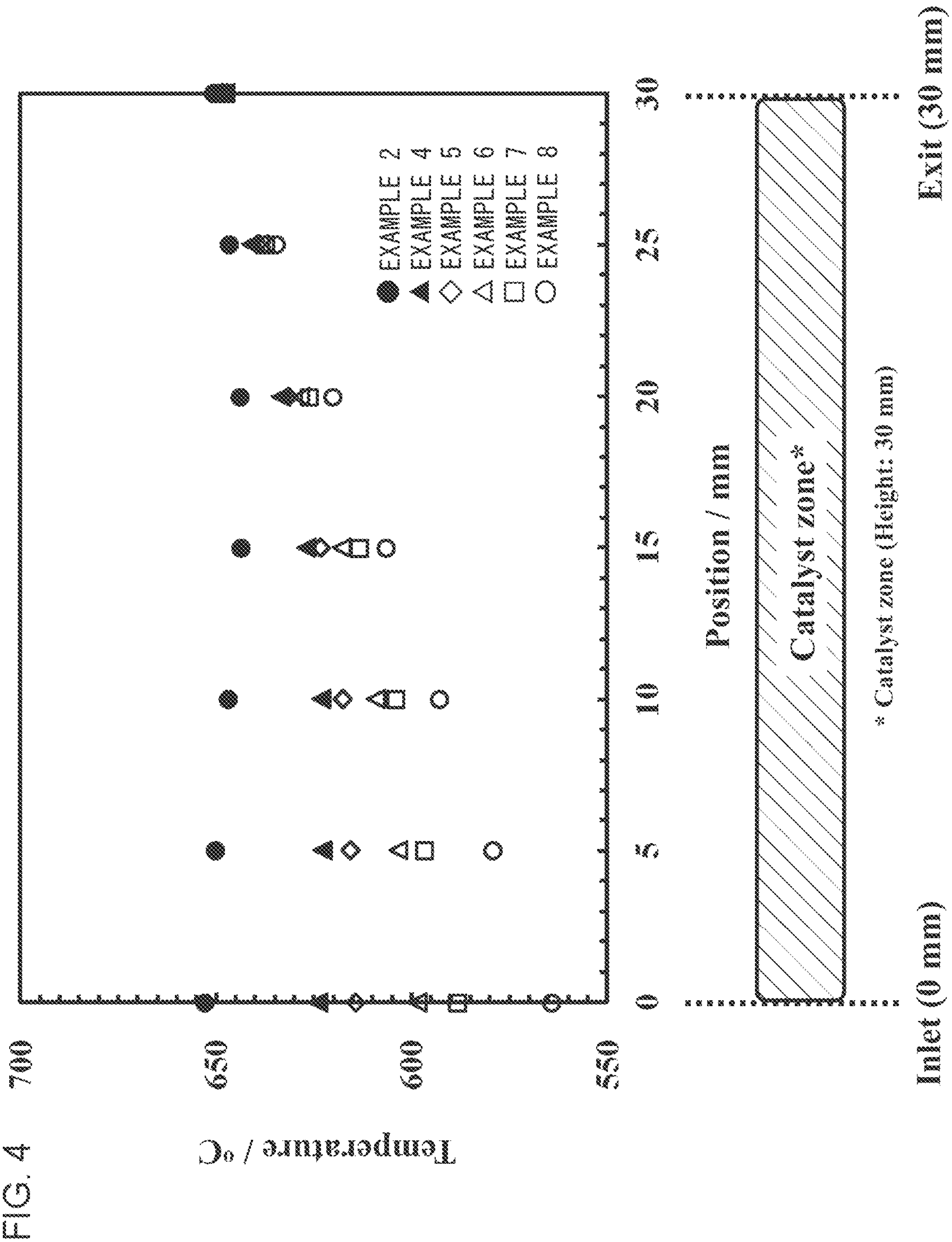
FIG. 4 is a diagram illustrating temperature distribution of catalyst zones in the performance evaluation test of the individual composite catalysts of Examples 2, 4 to 8.

The cylindrical P(0.2)-Fe—Ga—Al-MFI/AE200 catalyst prepared according to the aforementioned procedures was granulated to a length of 1.0 to 2.0 mm, thereby preparing a catalyst sample for performance evaluation. The performance evaluation test was conducted in a fixed bed flow type reactor (see FIG. 1), on the basis of a catalytic cracking reaction of a light hydrocarbon feedstock (a 50/50 wt % mixture of n-pentane (n-$C_5H_{12}$) and n-hexane (n-$C_6H_{14}$)). The catalyst that amounts 3.5 mL was packed in a stainless steel reaction tube (made of SUS316) having an inner diameter of 8.0 mm, so as to make the catalyst zone 30 mm high, glass wool was packed to the front and rear of the catalyst zone, and an alumina bead was packed further to the front and rear thereof. The catalytic cracking reaction was conducted under reaction conditions including an average temperature of the catalyst zone of about 650° C. (so as to maintain the entire portion of the catalyst zone at about 650° C., see FIGS. 3 and 4), a pressure of 0.15 MPa, and a liquid hourly space velocity (LHSV) of the light hydrocarbon feedstock of 6.0 $h^{-1}$ (supply flow rate of light hydrocarbon: 0.35 mL/min). Two hours after the start of the reaction, gas phase product and liquid phase product were sampled and analyzed by gas chromatography to determine one-pass conversion rate (wt %) of the light hydrocarbon feedstock and selectivity (wt %) of product, which were used as indices of catalyst performance. Note that, in the present disclosure, the one-pass conversion rate is defined as {(amount of fed feedstock−amount of unreacted feedstock)/ amount of fed feedstock}×100 [wt %], and the selectivity of product is defined as {amount of generated product/(amount of fed feedstock−amount of unreacted feedstock)}×100 [wt %].

Example 2

Method for Synthetizing Fe—Ga—Al-MFI Zeolite

A Na-type Fe—Ga—Al-MFI zeolite was synthesized in the same way as in Example 1. The zeolite was found, by X-ray fluorescence analysis, to have molar composition ratios of elements represented by Si/(Fe+Ga+Al)=91.5, Fe/(Fe+Ga+Al)=0.6, Ga/(Fe+Ga+Al)=0.1, and Al/(Fe+Ga+Al)=0.3 (see FIG. 2).

Method for Preparing Fe—Ga—Al-MFI/AE200 Catalyst

A Fe—Ga—Al-MFI/AE200 catalyst was synthesized in the same way as in Example 1. The catalyst was found, by X-ray fluorescence analysis, to have a weight composition represented by Fe—Ga—Al-MFI/AE200=65/35 [wt %/wt %] (see FIG. 2).

Method for Preparing P(1.0)-Fe—Ga—Al-MFI/AE200 Catalyst ($P_2O_5$ Loading: 1.0 wt %)

A phosphorus-modified Fe—Ga—Al-MFI/AE200 catalyst was prepared in the same way as in Example 1, except that the concentration of the aqueous diammonium hydrogen phosphate solution used for impregnation was changed to 2.0 mol/L (referred to as P(1.0)-Fe—Ga—Al-MFI/AE200 catalyst, hereinafter). The loading (weight composition) of the phosphorus compound was found, by fluorescent X-ray analysis, to be 1.0 wt % in terms of diphosphorus pentoxide ($P_2O_5$) (see FIG. 2).

Method for Performance Evaluation Test of P(1.0)-Fe—Ga—Al-MFI/AE200 Catalyst

The cylindrical P(1.0)-Fe—Ga—Al-MFI/AE200 catalyst prepared according to the aforementioned procedures was granulated to a length of 1.0 to 2.0 mm, thereby preparing a catalyst sample for performance evaluation. The performance evaluation test was conducted in the same way as in Example 1 (see FIG. 1).

Example 3

Method for Synthetizing Fe—Ga—Al-MFI Zeolite

A Na-type Fe—Ga—Al-MFI zeolite was synthesized in the same way as in Example 1. The zeolite was found, by X-ray fluorescence analysis, to have molar composition ratios of elements represented by Si/(Fe+Ga+Al)=91.5, Fe/(Fe+Ga+Al)=0.6, Ga/(Fe+Ga+Al)=0.1, and Al/(Fe+Ga+Al)=0.3 (see FIG. 2).

Method for Preparing Fe—Ga—Al-MFI/AE200 Catalyst

A Fe—Ga—Al-MFI/AE200 catalyst was synthesized in the same way as in Example 1. The catalyst was found, by X-ray fluorescence analysis, to have a weight composition represented by Fe—Ga—Al-MFI/AE200=65/35 [wt %/wt %] (see FIG. 2).

Method for Preparing P(1.0)-Fe—Ga—Al-MFI/AE200 Catalyst ($P_2O_5$ Loading: 1.0 wt %)

A phosphorus-modified Fe—Ga—Al-MFI/AE200 catalyst was prepared in the same way as in Example 2 (referred to as P(1.0)-Fe—Ga—Al-MFI/AE200 catalyst, hereinafter). The loading (weight composition) of the phosphorus compound was found, by fluorescent X-ray analysis, to be 1.0 wt % in terms of diphosphorus pentoxide ($P_2O_5$) (see FIG. 2).

Method for Performance Evaluation Test of P(1.0)-Fe—Ga—Al-MFI/AE200 Catalyst

The cylindrical P(1.0)-Fe—Ga—Al-MFI/AE200 catalyst prepared according to the aforementioned procedures was granulated to a length of 1.0 to 2.0 mm, thereby preparing a catalyst sample for performance evaluation. The performance evaluation test was conducted in the same way as in Example 1, except that steam was charged (25 wt %) in addition to the light hydrocarbon feedstock (see FIG. 1).

Comparative Example 1

Method for Synthetizing Fe—Ga—Al-MFI Zeolite

A Na-type Fe—Ga—Al-MFI zeolite was synthesized in the same way as in Example 1. The zeolite was found, by X-ray fluorescence analysis, to have molar composition ratios of elements represented by Si/(Fe+Ga+Al)=91.5, Fe/(Fe+Ga+Al)=0.6, Ga/(Fe+Ga+Al)=0.1, and Al/(Fe+Ga+Al)=0.3 (see FIG. 2).

Method for Preparing Fe—Ga—Al-MFI/AE200 Catalyst

A Fe—Ga—Al-MFI/AE200 catalyst was synthesized in the same way as in Example 1. The catalyst was found, by X-ray fluorescence analysis, to have a weight composition represented by Fe—Ga—Al-MFI/AE200=65/35 [wt %/wt %] (see FIG. 2).

Method for Performance Evaluation Test of Fe—Ga—Al-MFI/AE200 Catalyst

The cylindrical Fe—Ga—Al-MFI/AE200 catalyst prepared according to the aforementioned procedures was granulated to a length of 1.0 to 2.0 mm, thereby preparing a catalyst sample for performance evaluation. The performance evaluation test was conducted in the same way as in Example 1 (see FIG. 1).

FIG. 3 summarizes results of the performance test of the catalysts obtained in Comparative Example 1 and Examples 1 to 3. The Fe—Ga—Al-MFI/AE200 catalyst not modified with the phosphorus compound (Comparative Example 1) demonstrated a one-pass conversion rate of light hydrocarbon feedstock of 71.5 wt %, lower olefins selectivity of 51.0 wt % (total of ethylene, propylene, and butenes), and a selectivity to BTX of 17.5 wt % (total of benzene, toluene, and xylene). On the other hand, the P(0.2)-Fe—Ga—Al-MFI/AE200 catalyst (Example 1) with a 0.2 wt % load of $P_2O_5$ demonstrated the one-pass conversion rate improved up to 75.5 wt %, while maintaining the lower olefin selectivity (50.3 wt %) at a level equivalent to that in Comparative Example 1. The P(1.0)-Fe—Ga—Al-MFI/AE200 catalyst (Example 2) with the $P_2O_5$ load increased up to 1.0 wt % demonstrated the one-pass conversion rate improved up to 79.9 wt %, with the lower olefin selectivity (49.4 wt %) maintained at a level equivalent to that in Comparative Example 1. The BTX selectivity was found to be 18.0 to 19.9 wt %, indicating a slight increase from that in Comparative Example 1.

It was thus found from the results that, in the catalytic cracking reaction of the light hydrocarbon feedstock, use of the phosphorus-modified Fe—Ga—Al-MFI/$SiO_2$ composite catalyst can provide an effect of increasing the feedstock conversion rate, without significantly affecting the product selectivity. It was also confirmed, from the reaction test with use of the phosphorus-modified Fe—Ga—Al-MFI/$SiO_2$ composite catalyst combined with wt % of steam to lower the partial pressure of the feedstock (Example 3), that production of lower olefins was further promoted, demonstrating the selectivity improved up to 58.2 wt %.

Example 4

Method for Synthetizing Fe—Ga—Al-MFI Zeolite

A Na-type Fe—Ga—Al-MFI zeolite was synthesized in the same way as in Example 1. The zeolite was found, by X-ray fluorescence analysis, to have molar composition ratios of elements represented by Si/(Fe+Ga+Al)=91.5, Fe/(Fe+Ga+Al)=0.6, Ga/(Fe+Ga+Al)=0.1, and Al/(Fe+Ga+Al)=0.3 (see FIG. 2).

Method for Preparing Fe—Ga—Al-MFI/AE200 Catalyst

A Fe—Ga—Al-MFI/AE200 catalyst was synthesized in the same way as in Example 1. The catalyst was found, by X-ray fluorescence analysis, to have a weight composition represented by Fe—Ga—Al-MFI/AE200=65/35 [wt %/wt %] (see FIG. 2).

Method for Preparing P(1.0)-Fe—Ga—Al-MFI/AE200 Catalyst ($P_2O_5$ Loading: 1.0 wt %)

A phosphorus-modified Fe—Ga—Al-MFI/AE200 catalyst was prepared in the same way as in Example 2 (referred to as P(1.0)-Fe—Ga—Al-MFI/AE200 catalyst, hereinafter). The loading (weight composition) of the phosphorus compound was found, by fluorescent X-ray analysis, to be 1.0 wt % in terms of diphosphorus pentoxide ($P_2O_5$) (see FIG. 2).

Method for Performance Evaluation Test of P(1.0)-Fe—Ga—Al-MFI/AE200 Catalyst

The cylindrical P(1.0)-Fe—Ga—Al-MFI/AE200 catalyst prepared according to the aforementioned procedures was granulated to a length of 1.0 to 2.0 mm, thereby preparing a catalyst sample for performance evaluation. The performance evaluation test was performed in the same way as in Example 1 (see FIG. 1), except that the average temperature of the catalyst zone was set to about 631° C. (with the inlet temperature of the catalyst zone maintained at about 624° C., and with the exit temperature maintained at about 648° C., see FIG. 4).

Example 5

Method for Synthetizing Fe—Ga—Al-MFI Zeolite

A Na-type Fe—Ga—Al-MFI zeolite was synthesized in the same way as in Example 1. The zeolite was found, by X-ray fluorescence analysis, to have molar composition ratios of elements represented by Si/(Fe+Ga+Al)=91.5, Fe/(Fe+Ga+Al)=0.6, Ga/(Fe+Ga+Al)=0.1, and Al/(Fe+Ga+Al)=0.3 (see FIG. 2).

Method for Preparing Fe—Ga—Al-MFI/AE200 Catalyst

A Fe—Ga—Al-MFI/AE200 catalyst was synthesized in the same way as in Example 1. The catalyst was found, by X-ray fluorescence analysis, to have a weight composition represented by Fe—Ga—Al-MFI/AE200=65/35 [wt %/wt %] (see FIG. 2).

Method for Preparing P(1.0)-Fe—Ga—Al-MFI/AE200 Catalyst ($P_2O_5$ Loading: 1.0 wt %)

A phosphorus-modified Fe—Ga—Al-MFI/AE200 catalyst was prepared in the same way as in Example 2 (referred to as P(1.0)-Fe—Ga—Al-MFI/AE200 catalyst, hereinafter). The loading (weight composition) of the phosphorus compound was found, by fluorescent X-ray analysis, to be 1.0 wt % in terms of diphosphorus pentoxide ($P_2O_5$) (see FIG. 2).

Method for Performance Evaluation Test of P(1.0)-Fe—Ga—Al-MFI/AE200 Catalyst

The cylindrical P(1.0)-Fe—Ga—Al-MFI/AE200 catalyst prepared according to the aforementioned procedures was granulated to a length of 1.0 to 2.0 mm, thereby preparing a catalyst sample for performance evaluation. The performance evaluation test was performed in the same way as in Example 1 (see FIG. 1), except that the average temperature of the catalyst zone was set to about 627° C. (with the inlet temperature of the catalyst zone maintained at about 614° C., and with the exit temperature maintained at about 648° C., see FIG. 4).

Example 6

Method for Synthetizing Fe—Ga—Al-MFI Zeolite

A Na-type Fe—Ga—Al-MFI zeolite was synthesized in the same way as in Example 1. The zeolite was found, by X-ray fluorescence analysis, to have molar composition ratios of elements represented by Si/(Fe+Ga+Al)=91.5, Fe/(Fe+Ga+Al)=0.6, Ga/(Fe+Ga+Al)=0.1, and Al/(Fe+Ga+Al)=0.3 (see FIG. 2).

Method for Preparing Fe—Ga—Al-MFI/AE200 Catalyst

A Fe—Ga—Al-MFI/AE200 catalyst was synthesized in the same way as in Example 1. The catalyst was found, by X-ray fluorescence analysis, to have a weight composition represented by Fe—Ga—Al-MFI/AE200=65/35 [wt %/wt %] (see FIG. 2).

Method for Preparing P(1.0)-Fe—Ga—Al-MFI/AE200 Catalyst ($P_2O_5$ Loading: 1.0 wt %)

A phosphorus-modified Fe—Ga—Al-MFI/AE200 catalyst was prepared in the same way as in Example 2 (referred to as P(1.0)-Fe—Ga—Al-MFI/AE200 catalyst, hereinafter). The loading (weight composition) of the phosphorus compound was found, by fluorescent X-ray analysis, to be 1.0 wt % in terms of diphosphorus pentoxide ($P_2O_5$) (see FIG. 2).

Method for Performance Evaluation Test of P(1.0)-Fe—Ga—Al-MFI/AE200 Catalyst

The cylindrical P(1.0)-Fe—Ga—Al-MFI/AE200 catalyst prepared according to the aforementioned procedures was granulated to a length of 1.0 to 2.0 mm, thereby preparing a catalyst sample for performance evaluation. The performance evaluation test was performed in the same way as in Example 1 (see FIG. 1), except that the average temperature of the catalyst zone was set to about 621° C. (with the inlet temperature of the catalyst zone maintained at about 599° C., and with the exit temperature maintained at about 649° C., see FIG. 4).

Example 7

Method for Synthetizing Fe—Ga—Al-MFI Zeolite

A Na-type Fe—Ga—Al-MFI zeolite was synthesized in the same way as in Example 1. The zeolite was found, by X-ray fluorescence analysis, to have molar composition ratios of elements represented by Si/(Fe+Ga+Al)=91.5, Fe/(Fe+Ga+Al)=0.6, Ga/(Fe+Ga+Al)=0.1, and Al/(Fe+Ga+Al)=0.3 (see FIG. 2).

Method for Preparing Fe—Ga—Al-MFI/AE200 Catalyst

A Fe—Ga—Al-MFI/AE200 catalyst was synthesized in the same way as in Example 1. The catalyst was found, by X-ray fluorescence analysis, to have a weight composition represented by Fe—Ga—Al-MFI/AE200=65/35 [wt %/wt %] (see FIG. 2).

Method for Preparing P(1.0)-Fe—Ga—Al-MFI/AE200 Catalyst ($P_2O_5$ Loading: 1.0 wt %)

A phosphorus-modified Fe—Ga—Al-MFI/AE200 catalyst was prepared in the same way as in Example 2 (referred to as P(1.0)-Fe—Ga—Al-MFI/AE200 catalyst, hereinafter). The loading (weight composition) of the phosphorus compound was found, by fluorescent X-ray analysis, to be 1.0 wt % in terms of diphosphorus pentoxide ($P_2O_5$) (see FIG. 2).

Method for Performance Evaluation Test of P(1.0)-Fe—Ga—Al-MFI/AE200 Catalyst

The cylindrical P(1.0)-Fe—Ga—Al-MFI/AE200 catalyst prepared according to the aforementioned procedures was granulated to a length of 1.0 to 2.0 mm, thereby preparing a catalyst sample for performance evaluation. The performance evaluation test was performed in the same way as in Example 1 (see FIG. 1), except that the average temperature of the catalyst zone was set to about 616° C. (with the inlet temperature of the catalyst zone maintained at about 588° C., and with the exit temperature maintained at about 648° C., see FIG. 4).

Example 8

Method for Synthetizing Fe—Ga—Al-MFI Zeolite

A Na-type Fe—Ga—Al-MFI zeolite was synthesized in the same way as in Example 1. The zeolite was found, by X-ray fluorescence analysis, to have molar composition ratios of elements represented by Si/(Fe+Ga+Al)=91.5, Fe/(Fe+Ga+Al)=0.6, Ga/(Fe+Ga+Al)=0.1, and Al/(Fe+Ga+Al)=0.3 (see FIG. 2).

Method for Preparing Fe—Ga—Al-MFI/AE200 Catalyst

A Fe—Ga—Al-MFI/AE200 catalyst was synthesized in the same way as in Example 1. The catalyst was found, by X-ray fluorescence analysis, to have a weight composition represented by Fe—Ga—Al-MFI/AE200=65/35 [wt %/wt %] (see FIG. 2).

Method for Preparing P(1.0)-Fe—Ga—Al-MFI/AE200 Catalyst ($P_2O_5$ Loading: 1.0 wt %)

A phosphorus-modified Fe—Ga—Al-MFI/AE200 catalyst was prepared in the same way as in Example 2 (referred to as P(1.0)-Fe—Ga—Al-MFI/AE200 catalyst, hereinafter). The loading (weight composition) of the phosphorus compound was found, by fluorescent X-ray analysis, to be 1.0 wt % in terms of diphosphorus pentoxide ($P_2O_5$) (see FIG. 2).

Method for Performance Evaluation Test of P(1.0)-Fe—Ga—Al-MFI/AE200 Catalyst

The cylindrical P(1.0)-Fe—Ga—Al-MFI/AE200 catalyst prepared according to the aforementioned procedures was granulated to a length of 1.0 to 2.0 mm, thereby preparing a catalyst sample for performance evaluation. The performance evaluation test was conducted in the same way as in Example 1 (see FIG. 1), except that the average temperature of the catalyst zone was set to about 607° C. (with the inlet temperature of the catalyst zone maintained at about 564° C., and the exit temperature at about 649° C., see FIG. 4).

Figure 5:
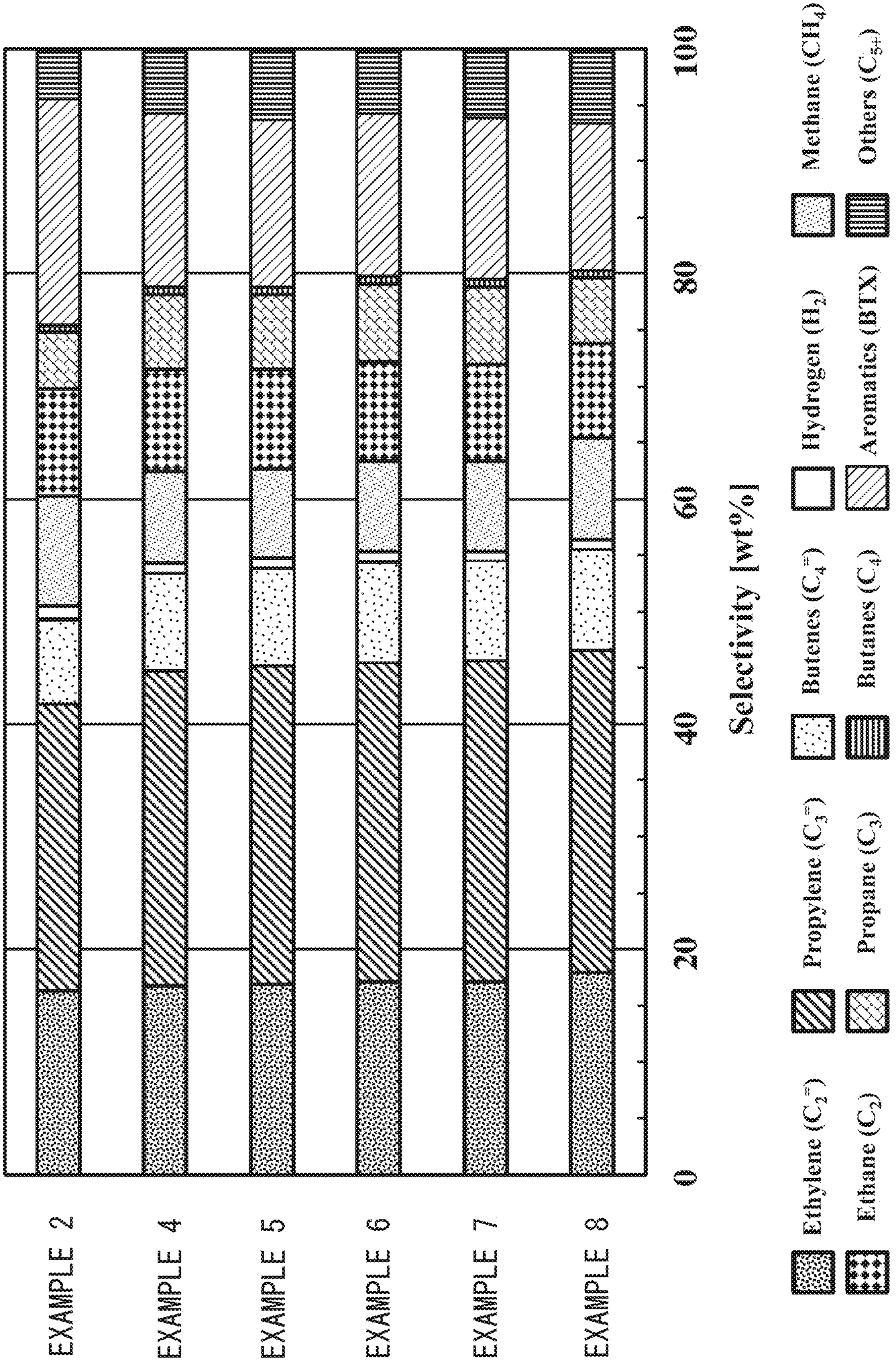
FIG. 5 is a diagram illustrating results of the performance evaluation test of the individual composite catalysts of Examples 2, 4 to 8.

The catalyst performance in Example 2 and Examples 4 to 8 is summarized in FIGS. 5 and 6. Example 2 demonstrates a result of reaction test obtained under a nearly isothermal condition, with the temperature of the catalyst zone maintained at about 650° C. over the entire range (3 cm height) (see FIG. 4). On the other hand, Examples 4 to 8 demonstrate results of reaction test obtained under an intentionally gradated temperature condition, with the catalyst zone exit temperature maintained at about 650° C., and with the inlet temperature set to lower than the exit temperature within the range from 564 to 624° C. Having demonstrated equivalent levels of one-pass conversion rate from 77.4 to 79.9 wt %, these Examples were found to differ in the product distribution, wherein the lower the inlet temperature, the more the lower olefin selectivity improved, and the more the BTX selectivity suppressed (see FIGS. 5 and 6).

It was thus found from the results that, in the catalytic cracking reaction of the light hydrocarbon feedstock with use of the phosphorus-modified Fe—Ga—Al-MFI/$SiO_2$ composite catalyst, provision of the temperature gradient to the catalyst zone with the inlet temperature set low, can produce the lower olefins more selectively.

Example 9

Method for Synthetizing Fe—Ga—Al-MFI Zeolite

A Na-type Fe—Ga—Al-MFI zeolite was synthesized in the same way as in Example 1. The zeolite was found, by X-ray fluorescence analysis, to have molar composition ratios of elements represented by Si/(Fe+Ga+Al)=91.5, Fe/(Fe+Ga+Al)=0.6, Ga/(Fe+Ga+Al)=0.1, and Al/(Fe+Ga+Al)=0.3 (see FIG. 7).

Method for Preparing Fe—Ga—Al-MFI/AE380 Catalyst

A Fe—Ga—Al-MFI/AE380 catalyst was prepared in the same way as in Example 1, except that silica powder (AEROSIL (registered trademark) 380, Nippon Aerosil Co., Ltd., BET specific surface area 380 $m^2/g$) was used as a binder. The catalyst was found, by X-ray fluorescence analysis, to have a weight composition represented by Fe—Ga—Al-MFI/AE380=65/35 [wt %/wt %] (see FIG. 7).

Method for Preparing P(1.0)-Fe—Ga—Al-MFI/AE380 Catalyst ($P_2O_5$ Loading: 1.0 wt %)

A phosphorus-modified Fe—Ga—Al-MFI/AE380 catalyst (referred to as P(1.0)-Fe—Ga—Al-MFI/AE380 catalyst, hereinafter) was prepared in the same way as in Example 2, with use of the cylindrical Fe—Ga—Al-MFI/AE380 catalyst prepared according to the aforementioned procedures. The loading (weight composition) of the phosphorus compound was found, by fluorescent X-ray analysis, to be 1.0 wt % in terms of diphosphorus pentoxide ($P_2O_5$) (see FIG. 7).

Method for Performance Evaluation Test of P(1.0)-Fe—Ga—Al-MFI/AE380 Catalyst

The cylindrical P(1.0)-Fe—Ga—Al-MFI/AE380 catalyst prepared according to the aforementioned procedures was granulated to a length of 1.0 to 2.0 mm, thereby preparing a catalyst sample for performance evaluation. The performance evaluation test was conducted in the same way as in Example 1 (see FIG. 1), except that the average temperature of the catalyst zone was set to about 604° C. (with the inlet temperature of the catalyst zone maintained at about 564° C., and the exit temperature at about 650° C.).

Example 10

Method for Synthetizing Fe—Ga—Al-MFI Zeolite

A Na-type Fe—Ga—Al-MFI zeolite was synthesized in the same way as in Example 1. The zeolite was found, by X-ray fluorescence analysis, to have molar composition ratios of elements represented by Si/(Fe+Ga+Al)=91.5, Fe/(Fe+Ga+Al)=0.6, Ga/(Fe+Ga+Al)=0.1, and Al/(Fe+Ga+Al)=0.3 (see FIG. 7).

Method for Preparing Fe—Ga—Al-MFI/HDK-T40 Catalyst

A proton-type Fe—Ga—Al-MFI zeolite/silica composite catalyst (referred to as Fe—Ga—Al-MFI/HDK-T40 catalyst, hereinafter) was prepared in the same way as in Example 1, except that silica powder (HDK (registered trademark)-T40, from Wacker Chemicals (China) Ltd., BET specific surface area: 387 $m^2/g$) was used as the binder. The catalyst was found, by X-ray fluorescence analysis, to have a weight composition represented by Fe—Ga—Al-MFI/HDK-T40=65/35 [wt %/wt %] (see FIG. 7).

Method for Preparing P(1.0)-Fe—Ga—Al-MFI/HDK-T40 Catalyst ($P_2O_5$ Loading: 1.0 wt %)

A phosphorus-modified Fe—Ga—Al-MFI/HDK-T40 catalyst (referred to as P(1.0)-Fe—Ga—Al-MFI/HDK-T40 catalyst, hereinafter) was prepared in the same way as in Example 2, with use of the cylindrical Fe—Ga—Al-MFI/HDK-T40 catalyst prepared according to the aforementioned procedures. The loading (weight composition) of the phosphorus compound was found, by fluorescent X-ray analysis, to be 1.0 wt % in terms of diphosphorus pentoxide ($P_2O_5$) (see FIG. 7).

Method for Performance Evaluation Test of P(1.0)-Fe—Ga—Al-MFI/HDK-T40 Catalyst

The cylindrical P(1.0)-Fe—Ga—Al-MFI/HDK-T40 catalyst prepared according to the aforementioned procedures was granulated to a length of 1.0 to 2.0 mm, thereby preparing a catalyst sample for performance evaluation. The performance evaluation test was conducted in the same way as in Example 1 (see FIG. 1), except that the average temperature of the catalyst zone was set to about 606° C. (with the inlet temperature maintained at about 565° C., and the exit temperature at about 648° C.).

FIG. 8 is a table summarizing results of catalyst performance test in Examples 8, 9, and 10. Compared with the P(1.0)-Fe—Ga—Al-MFI/AE200 catalyst (Example 8) with use of the silica binder having a BET specific surface area of 200 $m^2/g$, the P(1.0)-Fe—Ga—Al-MFI/AE380 catalyst (Example 9) and the P(1.0)-Fe—Ga—Al-MFI/HDK-40 catalyst (Example 10), both with use of silica binders having larger BET specific surface areas (380 to 387 $m^2/g$) demonstrated the one-pass conversion rate improved up to 83.2 to 83.9 wt %, while maintaining the lower olefin selectivity (53.2 to 55.0 wt %) and the BTX selectivity (13.5 to 16.0 wt %) at the equivalent levels.

It was thus found from the results that, in the catalytic cracking reaction of the light hydrocarbon feedstock, use of the phosphorus-modified Fe—Ga—Al-MFI/$SiO_2$ composite catalyst, combined with the silica binder having a large specific surface area, can provide an effect of increasing the feedstock conversion rate, without significantly affecting the product selectivity.

The embodiments of the present disclosure have been detailed. All of the aforementioned embodiments merely illustrate specific examples for carrying out the present invention. The contents of the embodiments do not limit the technical scope of the present invention, instead allowing numerous design changes such as modification, addition, and deletion of constituents, without departing from the spirit of the present invention specified in the claims. While the contents allowed for such design modification have been emphasized with notations such as "... of this embodiment" or "in this embodiment ... ", any contents without such notations are allowed for the design modification. Also, any optional combinations of the aforementioned constituents are valid as modes of the present disclosure.

What is claimed is:

1. A composite catalyst comprising: a zeolite which is a crystalline aluminosilicate that contains gallium and iron, and has a skeletal structure of an 8- to 12-membered ring; silicon dioxide as a binder; and diphosphorus pentoxide, wherein the zeolite has an acid density, which is defined as a molar ratio of silicon relative to the sum of iron, gallium, and aluminum, of 75.0 to 200.0, has a molar ratio of gallium relative to the sum of iron, gallium, and aluminum, of 0.1 to 0.4, and has a molar ratio of iron relative to the sum of iron, gallium, and aluminum, of 0.2 to 0.6, wherein the silicon dioxide has a BET surface area of 380 to 400 $m^2/g$.

2. The composite catalyst according to claim 1, containing 0.1 to 5.0 wt % of the diphosphorus pentoxide.

3. The composite catalyst according to claim 1, containing 5 to 50 wt % of the silicon dioxide.

4. A method for producing the composite catalyst according to claim 1, the method comprising a hydrothermal synthesis step, a molding step, an ion exchange step, and a phosphorus modification step.

5. A method for producing lower olefins, the method comprising feeding a hydrocarbon feedstock to an inlet of a catalyst zone that contains the composite catalyst according to claim 1, and obtaining the lower olefins from an exit of the catalyst zone, while controlling a temperature difference of 10° C. to 200° C. between the inlet and the exit.

6. A composite catalyst comprising: a zeolite which is a crystalline aluminosilicate that contains iron but no gallium, and has a skeletal structure of an 8- to 12-membered ring; silicon dioxide as a binder; and diphosphorus pentoxide, wherein the zeolite has an acid density, which is defined as a molar ratio of silicon relative to the sum of iron and aluminum, of 75.0 to 200.0, and has a molar ratio of iron relative to the sum of iron and aluminum, of 0.4 to 0.7, wherein the silicon dioxide has a BET surface area of 380 to 400 $m^2/g$.

7. The composite catalyst according to claim 6, containing 0.1 to 5.0 wt % of the diphosphorus pentoxide.

8. The composite catalyst according to claim 6, containing 5 to 50 wt % of the silicon dioxide.

* * * * *